United States Patent [19]
Detty

[11] 4,084,584
[45] Apr. 18, 1978

[54] KNEE SLEEVE

[76] Inventor: Garnett E. Detty, 525 General Muhlenberg Rd., King of Prussia, Pa. 19406

[21] Appl. No.: 732,554

[22] Filed: Oct. 15, 1976

[51] Int. Cl.² .............................................. A61F 3/00
[52] U.S. Cl. ................................. 128/80 C; 128/165; 2/24
[58] Field of Search ................... 128/80 C, 80 R, 165, 128/87 R; 2/22, 24

[56] References Cited

U.S. PATENT DOCUMENTS

| | | | |
|---|---|---|---|
| 2,858,540 | 11/1958 | Morrison | 2/24 |
| 3,046,981 | 7/1962 | Biggs, Jr. et al. | 128/80 C |
| 3,189,919 | 6/1965 | Chase | 2/24 X |
| 3,406,406 | 10/1968 | Lutz | 2/24 |
| 3,934,583 | 1/1976 | Hollingshead et al. | 128/165 |

FOREIGN PATENT DOCUMENTS 101,132   9/1961   Denmark ........................ 128/80 C

*Primary Examiner*—John D. Yasko
*Attorney, Agent, or Firm*—Caesar, Rivise, Bernstein & Cohen, Ltd.

[57] ABSTRACT

A sleeve adapted to be placed over the knee, said sleeve being configured to anatomically conform to the thigh, knee and upper calf, said sleeve comprising a resilient elastomeric foam sheath having a fabric covering, said elastomeric foam being adapted to contact the body, said sheath being formed from two pieces, with the first piece being configured to encircle the front and sides of the leg in the area of the knee and the second piece being secured to said first piece by a pair of spaced, substantially parallel seams, said seams being on opposite sides of the center of the rear of the leg and knee. The sleeve can also include an opening over the patella, with a pad secured around the outer perimeter of the opening, said pad being adapted to contact the outer edge of the patella, and restrict the patella from lateral movement.

8 Claims, 8 Drawing Figures

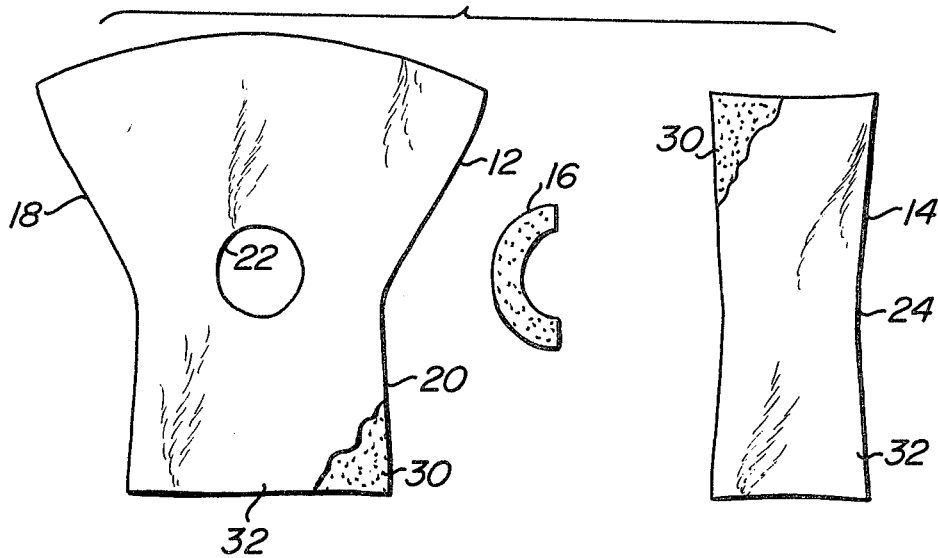
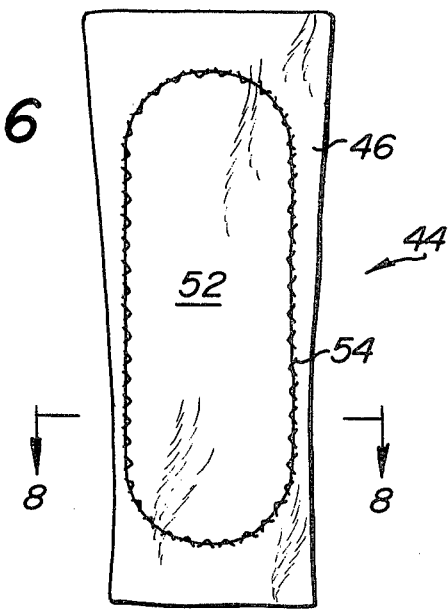
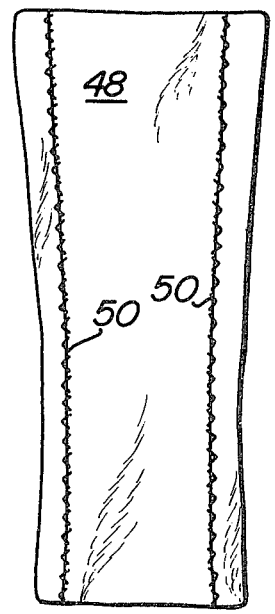
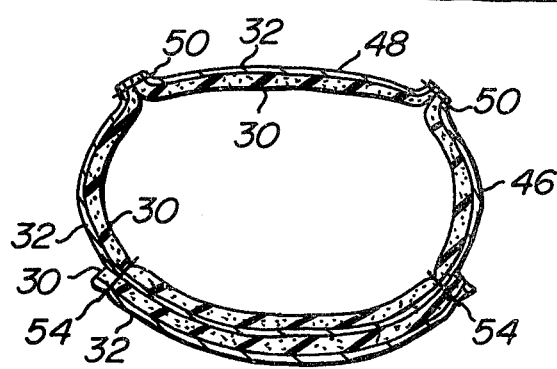

KNEE SLEEVE

This invention relates to a knee sleeve, and more particularly, to a sleeve that is particularly adapted to restrain the knee during normal and athletic activities, and prevent the patella from moving during flexion of the knee.

Various devices have been developed to restrict the knee, especially during normal knee movements in the practice of athletics Most commonly, these devices are used on injured, unhealthy or congenital knee problems which exhibit atrophy or weakness. These problems can result from an athletic or other injury or through such problems as arthritis. Various devices have been developed to protect the damaged knee or to give comfort to the person who has a damaged or afflicted knee. Such devices are shown in U.S. Pat. Nos. 3,613,681, 3,092,110 and 3,677,265.

Applicant has developed a number of knee sleeves that have proven to be most effective for use on an afflicted knee. One of applicant's devices that has been in use prior to the instant invention comprised a sleeve formed from an elastomeric foam material, such as foamed neoprene, and had an outer covering of fabric, such as knitted nylon. In order to have the device closely conform to the knee, while at the same time restraining the knee, a pair of lateral cuts were made on opposite sides of the knee. This configured the device to conform to the position of a slightly bent knee, in that the upper portion of the device, that is, the portion above the patella was angled with respect to the lower portion at a large obtuse angle. A lateral seam was made at each of the lateral cuts. Additionally, a vertical seam was formed down the center of the back of the device.

This device has proven to be extremely effective in restraining an afflicted knee and in providing suitable warmth to the knee. In this connection, a number of other devices have been provided which supply warmth to the knee and its muscles, such as the devices disclosed in aforementioned U.S. Pat. Nos. 3,092,110 and 3,613,681. However, it has been found in actual use that the lateral seams and the center vertical seam are uncomfortable to the wearer during periods of activity. These seams have been found to irritate the wearer, especially if the wearer is an athlete.

In one aspect of this invention, the lateral seams and the center vertical seam have been eliminated. Instead, the knee sleeve has been configured anatomically to the knee, and instead of having the center vertical seam and the lateral seams, these seams have been replaced by a pair of spaced vertical seams which are on opposite sides of the center of the rear of the leg. The spaced lateral seams have been found to be much more comfortable to the wearer of the knee sleeve, and in addition, the knee sleeve of this invention has been found to be more durable, since the prior lateral seams have been found to be an area of extreme wear. By eliminating the lateral seams, the durability of the knee sleeve has been greatly increased. At the same time, the positioning of the spaced vertical seams is far more comfortable to the wearer.

In another aspect of the invention, a means is provided for preventing the patella from travelling laterally. The means will stabilize the normal position of the patella. This aspect of the invention was developed from a prior invention of the applicant, which prior invention was used to treat chondromalacia of the patellofemoral joint. This condition is defined as an irregular undersurface of the patella, which condition is painful and disabling when the knee is flexed and extended.

In applicant's prior invention, the chondromalacia was treated by placing an opening in a knee sleeve in the area of the patella. The opening was roughly 1½ inches (3.81 cm.) in diameter. This opening removes all pressure from the patella, and the patella is free to rise within the opening. With the pressure removed, the remaining pressures around the knee, particularly from the popliteal area, forces fluid to the underside, or irritated side, of the freed patella. This apparently elevates the patella and provides a lubricant for patella movement when the knee is flexed and extended.

The success of the patella opening in a knee sleeve has led to the development of the restrictor means used to prevent the patella from travelling laterally. Thus, the restrictor means will stabilize the normal position of the patella. Normally, the quadricep muscle group tightens, exerting a pull on the patella when the leg is straightened from a flexed position. In the normal knee, this is a balanced, well-engineered, coordinated action. However, in the abnormal, deranged, injured, unhealthy or congenital knee, the knee will exhibit atrophy and weakness in the vastus medialis muscle group, which group is on the inner half of the upper border of the patella. The vastus lateralis (externus) muscle group, which is on the outer half of the upper border of the patella, retains its strength longer, and consequently the balanced pull on the patella is negated.

Accordingly, when there is a knee problem such as that described above, when the knee is flexed and extended, the vastus lateralis pulls the patella not only upward but also outward. This is an extreme departure from the norm, and is extremely undesirable. The results can vary in intensity from minor to very severe lateral dislocation of the patella. In fact, this lateral movement is believed to be a contributing factor to chondromalacia of the patella, as described above.

The deranged mechanism pull is outward or lateral in almost all cases. One of the surgical techniques now used to correct the problem is the releasing of some of the vastus lateralis fascia attachment from the patella. The knee sleeve of this invention results in restraining the floating patella, without the necessity of surgery. The knee sleeve of this invention is particularly adapted for people engaging in athletics.

It is accordingly an object of this invention to provide a novel knee sleeve.

It is another object of this invention to provide a knee sleeve adapted to restrain a travelling patella.

These and other objects of the invention are accomplished by providing a sleeve adapted to be placed over the knee, said sleeve being configured to anatomically conform to the thigh, knee and upper calf, said sleeve comprising a resilient elastomeric foam sheath having a fabric covering, said elastomeric foam being adapted to contact the body, said sheath being formed from two pieces, with a first piece being configured to encircle the knee and sides of the leg in the area of the knee and the second piece being secured to said first piece by a pair of spaced, substantially parallel seams, said seams being on opposite sides of the center of the rear of the leg and knee.

Other objects and many of the attendant advantages of this invention will be readily appreciated as the same becomes better understood by reference to the follow- FIG. 1 is a front elevational view of the knee sleeve of this invention, as shown on a right leg;

FIG. 5 is an exploded plan view of the elements of the knee sleeve of FIG. 1;

FIG. 6 is a front elevational view of a modified embodiment of the knee sleeve of this invention;

FIG. 7 is a rear elevational view of the knee sleeve of FIG. 6; and,

FIG. 8 is an enlarged sectional view taken along the line 8—8 of FIG. 6.

Figures 1, 2, 3, 4:
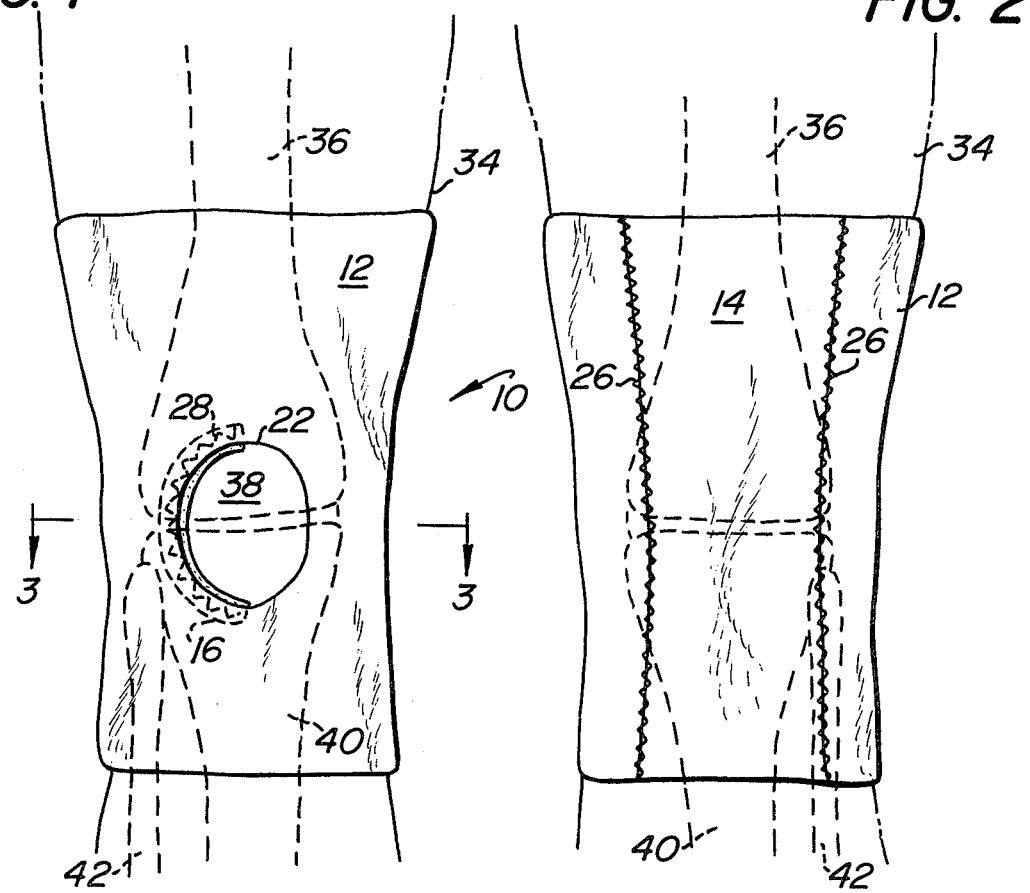
FIG. 2 is a rear elevational view of the knee sleeve of FIG. 1.
FIG. 3 is a sectional view taken along the line 3—3 of FIG. 1.
FIG. 4 is an enlarged sectional view taken in the area 4 of FIG. 3.

Referring now in greater detail to the various figures of the drawings wherein like reference characters refer to like parts, a knee sleeve embodying the present invention is generally shown at 10 in FIG. 1. As seen in FIG. 5, sleeve 10 comprises a front section 12, a rear panel 14 and a restrictor pad 16.

Referring still to FIG. 5, it is seen that the front section 12 includes an upper portion 18 and a lower portion 20. Lower portion 20 is basically rectangular in shape, but is tapered inwardly slightly in going from the bottom to the top of the portion. The upper portion 18 flares outwardly from the top of lower portion 20. The upper edge of portion 18 is slightly convex. An opening 22 is formed in front section 12, near the middle thereof.

Rear panel 14 is basically rectangular, but is tapered slightly between the outer ends and its center 24. The overall shape of panel 14 simulates an hour glass.

Restrictor pad 16 is semicircular in shape. Pad 16 is made from a resilient, but firm, material, such as felt.

The knee sleeve 10 is assembled by stitching the edges of rear panel 14 to the outer edges of front panel 12, as shown at 26 in FIGS. 2 and 3. When the panels are stitched together, the knee sleeve 10 is in a shape to anatomically conform to the lower portion of the thigh, the knee joint and the upper portion of the calf. As seen in FIG. 1, the restrictor pad 16 is stitched to the interior of front panel 12 by stitching 28, and adjacent opening 22. The restrictor pad 16 is positioned adjacent the outer side of opening 22. Thus, when the knee sleeve is to be worn on the right leg, the restrictor pad is on the right hand side of the opening. Similarly, when the knee sleeve is to be worn on the left leg, the restrictor pad is positioned on the left side of the opening.

Panels 12 and 14 are formed from the same material, which material comprises a resilient elastomeric material 30 and a covering of a knit fabric 32. The resilient elastomeric foam material 30 can comprise any of the foams known to the art, such as rubber, neoprene, latex and polyurethane foams. The fabric is knit, so that it will have inherent elastic properties. Preferably, the fabric is formd from synthetic yarns, such as nylon, to aid in durability and abrasion resistance. However, natural fibers can also be used, such as cotton. Any of the knit fabrics known to the art can be used, such as circular knit fabrics and tricots. The fabric is bonded to the foam by any of the known processes, such as flame lamination or adhesive bonding.

The knee sleeve 10 is shown in FIGS. 1 and 2 as being positioned on the right leg 34. The bones of the right leg are shown in phantom, and include the femur or thighbone 36, the patella or knee cap 38, the tibia or shinbone 40 and the fibula 42. With the knee sleeve in place, it is seen that the patella 38 projects through opening 22 in front panel 12. As explained above, in my prior invention, the opening 22 was used to reduce the friction of the patella during flexion and extension of the knee when the patella is suffering from chondromalacia. Thus, the patella can move forwardly in the knee sleeve, since the pressure over the patella is removed. This permits fluid to flow behind the patella and lubricate the patella when the user of the knee sleeve is actively engaged in any activity requiring leg movement, such as cycling, jogging, tennis, football, etc.

The patella opening has been in use for more than a year, and has been found to be completely satisfactory in obviating the pain of chondromalacia. However, the use of the felt restrictor pad forms a part of this invention, and has just recently been tested. As pointed out above, it is believed that one of the causes of chondromalacia is a floating kneecap. The floating of the kneecap occurs when there is atrophy of the muscle group around the kneecap. This atrophy attacks the inner muscle group more seriously than the outer muscle group, and accordingly during flexion and extension, the outer muscle group exerts a pulling force on the kneecap, thereby pulling the kneecap outwardly. This results in extreme discomfort use of the leg, and in many cases, is completely disabling. The use of the restrictor pad 16 in combination with the patella opening 22 prevents the lateral outward movement of the kneecap during activity. Thus, the kneecap will be cushioned by the fluid beneath the kneecap, in view of the patella opening 22. The restriction of the restrictor pad 16 can prevent any lateral outward movement of the kneecap. Accordingly, the wearer of the knee sleeve can move with complete comfort, without any of the disabling effects of chondromalacia and/or floating kneecap. Again, it should be pointed out that the restrictor pad must be on the outside of the leg, and in the case of the right leg, on the right hand side of the knee sleeve, as shown in FIG. 1. In FIG. 4, the restrictive force of the pad 16 is shown in detail, and the abutment of the pad against the patella is shown.

One of the features of the invention is the fact that the foam resilient material is in contact with the skin of the wearer. It has been found that where there is a fabric lining on the interior of the knee sleeve, the knee sleeve will tend to slip during active use of the leg. However, there is sufficient friction between the foam and the skin of the leg to prevent any slippage during use.

One of the advantages of the prior art knee sleeves which included a fabric lining was that the knee sleeve could more easily be pulled in place. However, it has been found that merely having the fabric 32 on the outside is sufficient to allow for the easy application of the knee sleeve. In this connection, it has been found that the knee sleeve is best applied by turning it inside out, that is, having the fabric on the inside. The knee sleeve is then slid on the leg by having the lower end uppermost, and the sliding is continued until the lower end is at the position where it will ultimately rest when the knee sleeve is fully in place. The upper end of the sleeve, which at this point is lowermost, is then pulled upwardly, which results in turning the rubber side inwardly. This results in turning the knee sleeve to a condition where the correct or fabric side is outward, and places the larger end on the thigh, in the position shown in FIG. 1. To aid in applying the knee sleeve, lubricating powders, such as talcum, corn starch or baking soda, should be liberally applied to the leg on which the knee sleeve will be used.

A modified embodiment of the knee sleeve of this invention is generally shown at 44 in FIG. 6. Knee sleeve 44 includes a front panel 46 and a rear panel 48, which are identical in configuration to panels 12 and 14, respectively. The only difference is that there is no opening 22 in front panel 46. Rear panel 48 is secured to front panel 46 by substantially vertical stitching 50. Panels 46 and 48 are made of the same foam and fabric laminate as panels 12 and 14. Thus, the foam 30 is on the inner surface of the knee sleeve 46 and the fabric 32 is on the outer surface.

In knee sleeve 46, there is an overlay panel 52 that is stitched to front panel 46 by stitching 54. The overlay panel 52 is formed from the same foam and fabric laminate 30 and 32 as the other panels of the knee sleeve of this invention. As seen in FIG. 6, overlay panel 52 extends for substantially the entire height of the front of the knee sleeve 46. The purpose of the overlay panel is to provide additional warmth for the knee joint and additional impact and abrasion protection for the knee. The embodiment of the knee sleeve 46 is used where there is no problem with chondromalacia or floating kneecap. This embodiment enjoys the same advantages as embodiment 10 in connection with the positioning of the rear stitching 50.

The knee sleeve of embodiment 44 is applied in the same manner as knee sleeve 10. Thus, it is turned inside out, and the lower portion of the knee sleeve is first pulled on the leg. When the upper edge of the sleeve is at its final position, that is, below the knee, the upper portion of the knee sleeve, which is now lowermost, is pulled upwardly, thereby bringing the fabric side outward. The final position of the knee sleeve will be the same as that shown for embodiment 10 in FIG. 1.

The foam and fabric laminate of the knee sleeves of this invention can be used in any standard thicknesses, such as ⅛ inch (0.318 cm), 3/16 inch (0.476 cm.) or ¼ inch (0.635 cm.). The embodiment including the overlay 52 will normally be made in the ⅛ inch (0.318 cm.) thickness, with the overlay being the same thickness as the front panel 46 and the rear panel 48.

As seen in FIG. 5, the shapes of the front panel 12 and the rear panel 14 permit the knee sleeve of this invention to anatomically conform to the thigh, knee and upper calf. Panels 46 and 48 have the same configuration. The fabric laminated to the foam gives the foam dimensional stability, preserves the foam from deteriorating due to abrasion and aids in placing the knee sleeve on the knee. Having the rear seams 26 and 50 spaced from the center of the rear of the leg has been found to provide the most comfortable area for the seams. The prior center seam with the two lateral seams meeting at the center seam has been found to be uncomfortable during periods of activity. This discomfort is minimized by the placement of the seams of this invention.

Because of the inherent elasticity of the knee sleeve, the knee sleeve can fit a range of knee sizes. The sizes of the knee sleeve are generally determined by measuring the circumference of the knee. Once the circumference is measured, normally the lower thigh and upper calf will readily conform to the knee circumference. Generally, each different size of knee sleeve can accommodate a range of 1 or 2 inches (2.54 or 5.08 cms.) in knee circumference. The size of the patella does not vary significantly, and accordingly in substantially all sizes of knee sleeve, the patella opening 22 will be approximately 1½ inches (3.81 cms.) in diameter.

The patella restrictor 16 has been found to give a firm, but gentle restriction to the lateral movement of the patella. Thus, even though there is a certain inherent resiliency in the felt pad, the pad is sufficiently firm to prevent any significant lateral movement of the patella. Additionally, in view of the fact that the patella is floating on a cushion of knee fluid, by virtue of the patella opening 22, it does not take a significant force to restrain the lateral movement of the patella. As explained above, the restrictor pad 16 is always on the outside of the patella, as seen in FIG. 1 with respect to the right leg. Although the size of the restrictor pad 16 can be varied, the best results have been obtained by utilizing a restrictor pad that is ¼ to ½ inch (0.635 to 1.27 cm.) thick, 1 inch (2.54 cm.) wide and 3 inches (7.62 cm.) long.

Without further elaboration, the foregoing will so fully illustrate my invention, that others may, by applying current or future knowledge, readily adapt the same for use under various conditions of service.

What is claimed as the invention is:

1. A sleeve adapted to be placed over the knee, said sleeve being configured to anotomically conform to the thigh, knee and upper calf, said sleeve comprising a resilient elastomeric foam sheath having a fabric covering, said sheath being formed from two pieces, with a first piece being configured to encircle the knee and sides of the leg in the area of the knee and the second piece being secured to said first piece by a pair of spaced, substantially parallel seams, said seams being on opposite sides of the center of the leg and knee, an opening formed in the front of said sleeve, said opening being adapted to permit the patella to project therethrough when the sleeve is on a user's leg, and restrictor means adjacent said opening, said restrictor means being adapted to bear against the patella and to prevent the patella from moving when the sleeve is on a leg.

2. The sleeve of claim 1 wherein said restrictor means is positioned such that it will be laterally outward when the sleeve is worn on a leg.

3. The sleeve of claim 1 wherein said restrictor means is arcuate and is secured on the interior of said sleeve.

4. The sleeve of claim 1 wherein said restrictor means is formed from felt.

5. The sleeve of claim 1 wherein said elastomeric foam is on the interior of said sleeve, and is adapted to contact the leg during use.

6. The sleeve of claim 1 wherein said elastomeric material is neoprene foam.

7. The sleeve of claim 1 wherein said fabric is a knit fabric.

8. The sleeve of claim 7 wherein said knit fabric comprises nylon.

* * * * *